United States Patent
Ohtani et al.

[11] Patent Number: 6,038,925
[45] Date of Patent: *Mar. 21, 2000

[54] FOCAL TYPE ELECTROMAGNETIC ACOUSTIC TRANSDUCER AND FLAW DETECTION SYSTEM AND METHOD

[75] Inventors: Toshihiro Ohtani, Kanagawa-ken; Hirotsugu Ogi; Masahiko Hirao, both of Osaka, all of Japan

[73] Assignee: Ebara Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/044,929

[22] Filed: Mar. 20, 1998

[30] Foreign Application Priority Data

Mar. 21, 1997 [JP] Japan ............................ 9-087363

[51] Int. Cl.⁷ ........................................... G01N 9/24
[52] U.S. Cl. .................. 73/598; 73/598; 73/600
[58] Field of Search ................ 73/598, 579, 600, 73/620, 622, 624, 638, 643; 367/181, 187

[56] References Cited

U.S. PATENT DOCUMENTS

| | | |
|---|---|---|
| 4,434,663 | 3/1984 | Peterson et al. . |
| 4,452,086 | 6/1984 | Hüschelrath et al. . |
| 4,593,567 | 6/1986 | Isselstein et al. ......................... 73/643 |
| 4,777,824 | 10/1988 | Alers et al. . |
| 5,503,020 | 4/1996 | Mandracchia ............................ 73/643 |
| 5,608,164 | 3/1977 | MacLauchlan . |
| 5,608,691 | 3/1997 | MacLauchlan et al. ................. 367/140 |
| 5,760,307 | 6/1998 | Latimer et al. ........................... 73/643 |
| 5,808,202 | 9/1998 | Passarelli, Jr. ............................ 73/643 |

Primary Examiner—Hezron Williams
Assistant Examiner—Thuy Vinh Tran
Attorney, Agent, or Firm—Oblon, Spivak, McClelland, Maier & Neustadt, P.C.

[57] ABSTRACT

A focusing electromagnetic acoustic transducer is provided which comprises a pair of meander coils, three insulation sheets and a magnet. The meander coils are formed on both surfaces of one of the insulation sheets to be positioned such that the meander coils are coincident with each other, and they are covered with the other insulation sheets. Each of the meander coils comprises a plurality of coil segments wherein intervals between adjacent coil segments sequentially are varied from one end to the other end. The magnet is positioned above the layers consisting the meander coils and insulation sheets. The coil segments of each meander coil are straight lines in parallel with each others, sector shapes on respective circulars having the same center point, or generally circular shapes having the same center point.

16 Claims, 13 Drawing Sheets

Fig. 13B

FOCAL TYPE ELECTROMAGNETIC ACOUSTIC TRANSDUCER AND FLAW DETECTION SYSTEM AND METHOD

BACKGROUND OF THE INVENTION

The present invention relates to a focal type(or focusing) electromagnetic ultrasonic transducer for detecting flaws on a surface of an object made of a conductive material, and flaws and internal deteriorations of an object, caused by an applied load and/or heat. The present invention also relates to an ultrasonic flaw detection method with the focal type electromagnetic acoustic transducer.

As one of the prior art techniques of an ultrasonic flaw detection, Japanese Patent Public Disclosure (Kokai) No. 1-127950 (1989) discloses a focusing electromagnetic acoustic transducer. This focusing electromagnetic acoustic transducer comprises an array of a plurality of permanent magnets, which are arranged on a line sequentially from thicker ones to thinner ones, and a coil wound around the magnet array. The alternating magnets of the array have different polarities from each other and portions of the magnets having such different polarities form a plane. The coil passes along the plane containing the polarities of the magnet array and the magnets are bound into a bundle.

Since the focusing electromagnetic acoustic transducer has magnets arranged from the thickest to the thinnest in a line such that respective adjacent magnets have different polarities from each other, wave fronts of acoustic waves in the depth direction of an object become in focused and are thus capable of improving a temporal resolution and facilitating the detection of flaws within an object.

The focusing electromagnetic acoustic transducer configured as described above requires magnets to have a reduced thickness in order to generate acoustic waves at high frequencies to thereby provide excellent flaw detecting capabilities. However, with the use of such magnets having smaller thickness, the transducer is more susceptible to a lift-off influence, and a magnetic flux of a magnet intrudes into an immediately adjacent magnet and thus an effective magnetic field may not be formed. Accordingly, appropriate actions of the electromagnetic acoustic transducer may be prevented by making the magnets thinly.

Further, the focusing electromagnetic acoustic transducer generates SH waves. The SH waves induce a problem that they have a wide radiation distribution so that a sharp directivity cannot be realized even if the thickness of the permanent magnets is varied to narrow down the focus.

Japanese Patent Public Disclosure (Kokai) No. 1-248052 describes an ultrasonic transducer. The transducer also generates SH waves and hence gives rise to the same problem as above.

Each of Japanese Patent Public Disclosure (Kokai) Nos. 63-305245 and 64-10168 describes an elevation type electromagnetic acoustic transducer which has coils with a fixed pitch and flowing currents at different frequencies through the respective coils. The elevation type electromagnetic acoustic transducer, however, requires complicated signal processing and is susceptible to producing disturbed acoustic waves within a material or object.

SUMMARY OF THE INVENTION

The present invention has been made in view of the problems of the prior arts mentioned above, and its object is to provide a focal type (or focusing) of electromagnetic acoustic transducer which is capable of changing a focal point by narrowing down the depth of focus and/or varying the frequency to improve the performance of flaw detection and flaw evaluation and ensure stable high performance.

Another object of the present invention is to provide a system and method of an ultrasonic flaw detection, using a focusing electromagnetic acoustic transducer.

In order to achieve the first object, a focusing electromagnetic acoustic transducer according to the present invention comprises: a first insulation sheet; a pair of meander coils formed on both surfaces of the first insulation sheet to be positioned opposite to each other through the first insulation sheet so that the meander coils are coincident with each other, each of the meander coils comprising a plurality of coil segments wherein intervals between adjacent coil segments sequentially are varied from one end to the other end; second and third insulation sheets attached to said meander coils to sandwich them between the first and second insulation sheets and the first and third insulation sheets, respectively; and a a magnet having opposite surfaces exhibiting opposite magnetic poles, one of the surfaces being positioned above the second insulation sheet so as to provide a magnetic field in the direction substantially perpendicular to the surface of the second sheet.

In a preferred embodiment of the transducer according to the present invention, the coil segments of each of the meander coils are straight lines in parallel with each other, thereby the transducer constitutes a line focusing electromagnetic acoustic transducer. In a second embodiment of the transducer according to the present invention, the coil segments of each of the meander coils are sector shapes on respective circulars having the same center point, thereby the transducer constitutes a point focusing electromagnetic acoustic transducer. In a third embodiment of the transducer according to the present invention, the coil segments of each of the meander coils are generally circular shapes having the same center point, thereby the transducer constitutes a point focusing electromagnetic acoustic transducer.

It is preferable that all ends of the meander coils are extending through through holes formed in the first and second insulation sheet to connection terminals on the surface of the second insulation sheet, and one of the terminals being a common ground terminal for the meander coils.

The present invention also provides a system for detecting a flaw in an object which comprises: (a) an focusing electromagnetic acoustic transducer to be placed on the object comprising: a first insulation sheet; a pair of meander coils formed on both surfaces of the first insulation sheet to be positioned opposite to each other through the first insulation sheet so that the meander coils are coincident with each other, each of the meander coils comprising a plurality of coil segments wherein intervals between adjacent coil segments sequentially are varied from one end to the other end; second and third insulation sheets attached to the meander coils to sandwich them between the first and second insulation sheets and the first and third insulation sheets, respectively; and a magnet positioned above the second insulation sheet; (b) a source for supplying a high frequency current to one of the meander coils to transmit SV waves into the object, the frequency of the current being variable to vary a focal point in the object; and (c) a detection means for detecting a flaw in the object in accordance with amplitudes and phases of signals detected by the other meander coil.

The present invention further provides a method of detecting a flaw in an object comprising the steps of: preparing a focusing electromagnetic acoustic transducer having transmission and reception meander coils; placing the transducer on the object; supplying a high frequency current to the transmission meander coil to transmit SV waves into the object, the frequency of the current being varied in time sequence to change a position of a focal point of the transducer; and detecting a flaw in the object, if any, in accordance with amplitudes and phases of signals detected by the reception meander coil.

BRIEF DESCRIPTION OF THE DRAWINGS

FIGS. 1A–1C illustrate a structure of a line focusing electromagnetic acoustic transducer according to the present invention, where

FIGS. 5A and 5B illustrate a structure of a point focusing electromagnetic acoustic transducer according to the present invention, where

FIGS. 7A and 7B illustrate another point focusing electromagnetic acoustic transducer according to the present invention, where

DESCRIPTION OF THE PREFERRED EMBODIMENTS

The present invention will hereinafter be described in connection with several embodiments thereof with reference to the accompanying drawing.

Figure 1A:
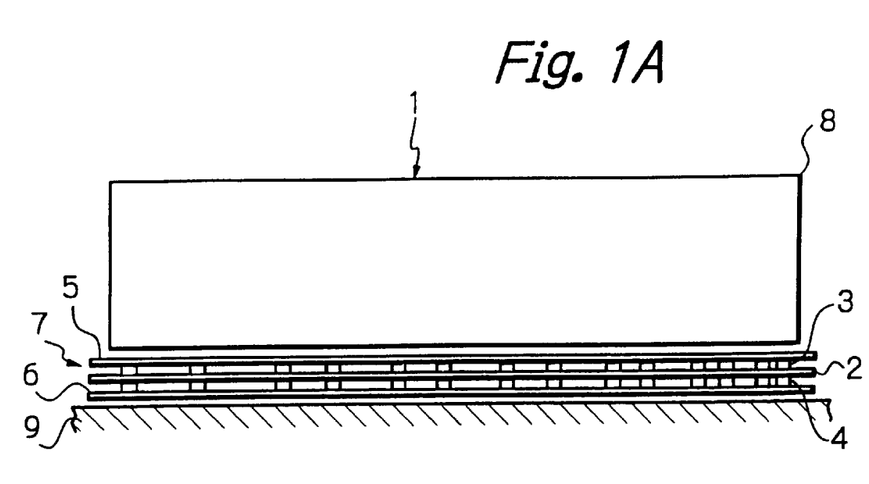
FIGS. 1A–1C are cross-sectional, side and bottom views of the acoustic transducer.
Figure 1B:
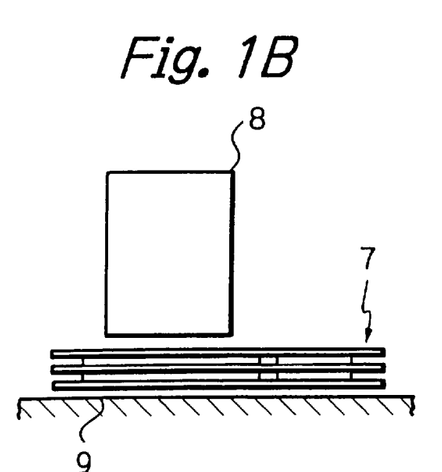
Figure 1C:
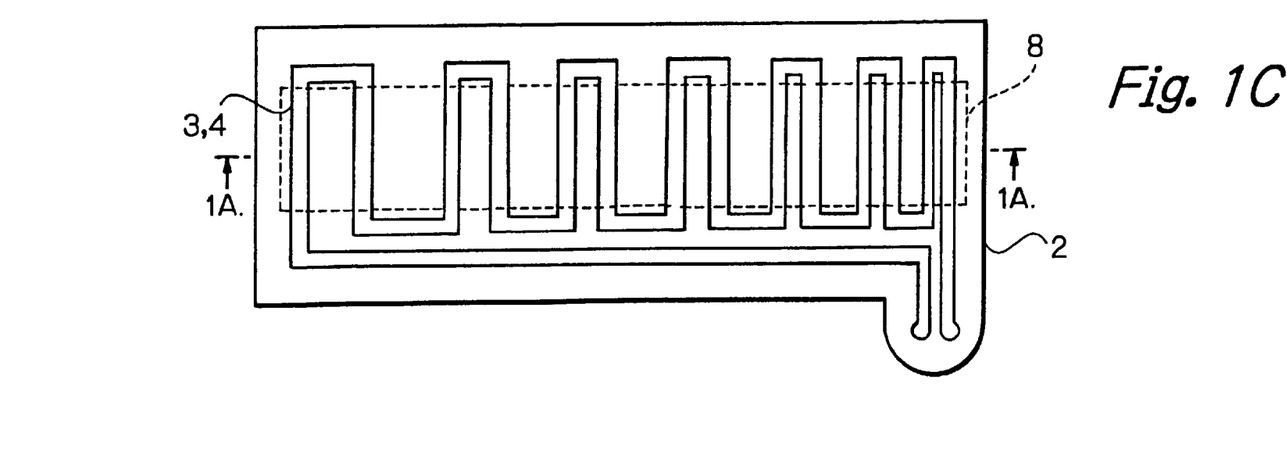

FIGS. 1A–1C illustrate explanatory views of a line focusing electromagnetic acoustic transducer according to the present invention, generally denoted by the reference numeral 1 therein. FIG. 1A is a cross-sectional view taken along a line A—A in FIG. 1C, FIG. 1B is a side-view, and FIG. 1C is a bottom view where a surface of a coil portion 7 of the acoustic transducer 1 is explanatorily illustrated. The acoustic transducer 1 comprises meander coils 3 and 4, made of a conductive material, disposed on both surfaces of an insulation sheet 2. The meander coils 3 and 4 are covered with insulation sheets 5 and 6, respectively, to form the coil portion 7. A single magnet (a permanent magnet or an electromagnet) 8 is positioned on the upper surface of the coil portion 7. The upper and lower meander coils 3 and 4 have the same geometry, and are arranged in parallel with each other on the upper and lower surfaces of the insulation sheet 2 to face to each other through the insulating sheet 2. Therefore, they are coincident with each other. In the coils 3 and 4, intervals between adjacent coil segments are sequentially varied from one side to the other. In FIG. 1C, the leftmost interval is the widest, and the intervals are gradually narrower from left to right. The numeral 9 denotes a target or object of a conductive material for flaw detection measurement.

Figure 2:
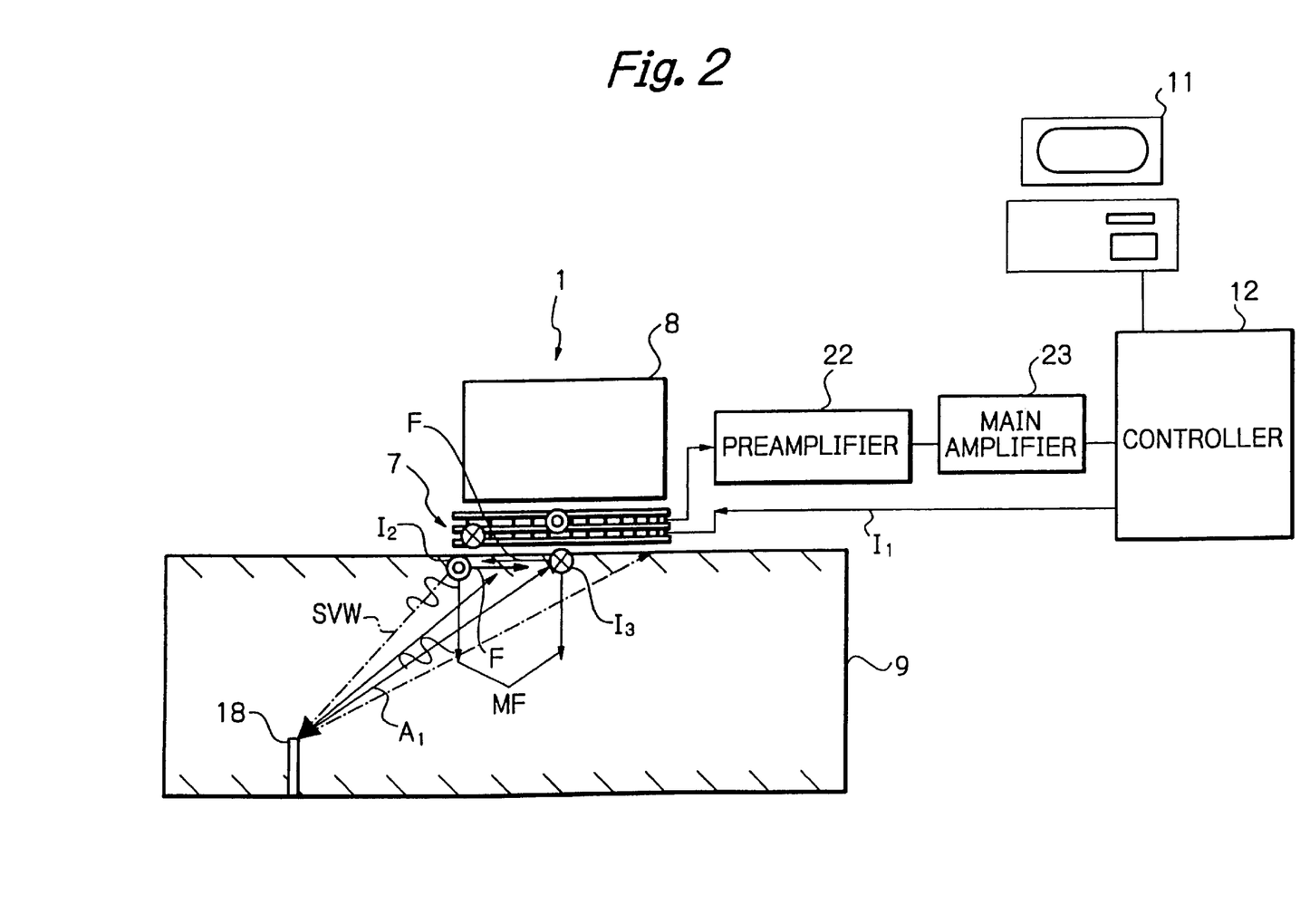
FIGS. 2–4 are diagrams for explaining operation principles of a flaw detection system using the electromagnetic acoustic transducer shown in FIG. 1.

FIG. 2 shows a flaw detection system employing the line focusing electromagnetic acoustic transducer shown in FIG. 1, wherein the numeral 11 denotes a personal computer, 12 a controller, 22 a preamplifier, and 23 a main amplifier. As illustrated in FIG. 2 (as well as FIG. 1), the acoustic transducer 1 is placed on the object 9 under a flaw detection measurement. The magnet 8 provides a static magnetic field MF in the depth direction of the object 9. In this state, when the lower meander coil 4 is supplied with a high frequency current $I_1$ from the controller 12 under a control of the personal computer 11, an eddy current $I_2$ is generated on the surface of the object 9 in the direction opposite to the current $I_1$. Then, Lorentz force F is produced by an interaction of the eddy current $I_2$ and the static magnetic field MF in accordance with the Fleming's left hand rule. The Lorentz force acts on free electrons in the material composing the object 9 to cause the free electrons to collide with ions and so on, exciting motion in the object 9 vertical to the directions of the static magnet field MF and the eddy current $I_2$ to generate an ultrasonic SV wave, SVW, for each coil segment.

The SVWs hemispherically propagate into the object 9, and reflect from a defect or flaw 18 such as a structure change, micro-crack or the like. In the reflected SVWs, some of them are directed in the directions indicated by arrows A1, and reach the surface portion of the object 9 directly under the transducer 1, where the static magnetic field MF exists. Therefore, the magnetic field temporally changes due to phase displacement of the acoustic waves. An eddy current $I_3$ is then generated in such a direction to prevent a magnetic field change. The produced eddy current $I_3$ is detected by the upper meander coil 3, and a signal indicative of the detected eddy current is sent to the controller 12 through the preamplifier 22 and the main amplifier 23. The controller 12 has a built-in super-heterodyne measuring system which only takes an amplitude and phase of the received signal so that measurement of the amplitude and phase can be made in a short time. The obtained amplitude and phase of the detected signal are provided to the personal computer 11, which calculates a position of the flaw 18 and displays the results.

Figure 3:
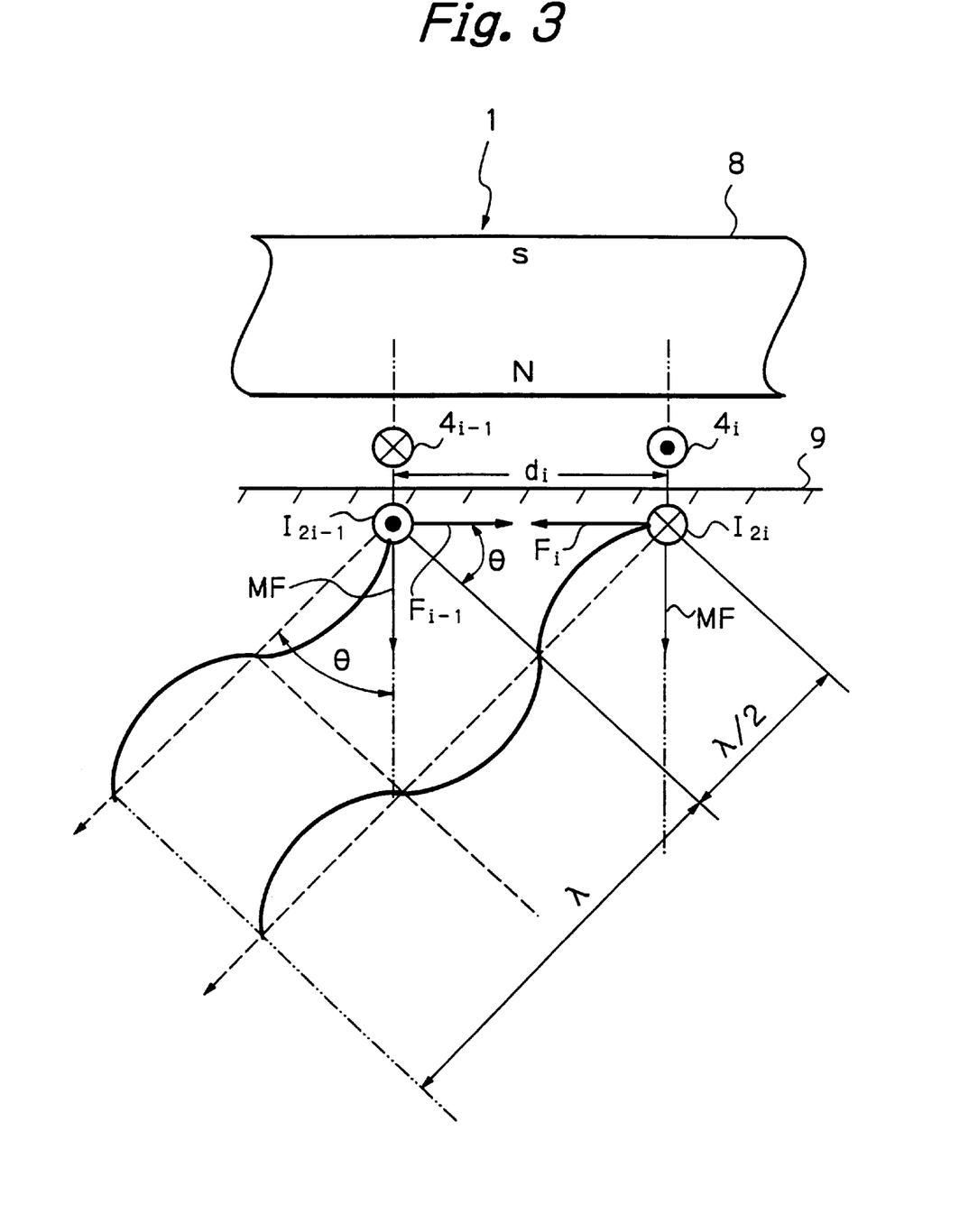

Next will be explained an operation of the system shown in FIG. 2 in more detail, by reference to FIGS. 3 and 4 as well as FIGS. 1 and 2. In adjacent coil segments $4_{i-1}$ and $4_i$ of the transmission meander coil 4 which is supplied the high frequency current I, from the controller 12, the current $I_1$ flows in the opposite directions from each other, so that eddy currents $I_{2i-1}$ and $I_{2i}$ generated by the adjacent coil segments $4_{i-1}$ and $4_i$, of course, flow in the opposite directions. Accordingly, as illustrated in FIG. 3, Lorentz forces $F_{i-1}$ and $F_i$ generated beneath the adjacent coil segments are forces out of phase by 180°, and thus ultrasonic waves generated thereby are also out of phase by 180° as shown in FIG. 3. In this case, it is assumed that an angle from the wave fronts of the ultrasonic waves or SVWs formed by the meander coil 4, in which the adjacent coil segments have the widest interval at one side and gradually narrower intervals toward the other side to the surface of the object 9, is θ. The relationship among the angle θ, interval di between the adjacent coil segments $4_{i-1}$ and $4_i$, and wavelength k of the ultrasonic waves is expressed by the following equation (1):

$$\sin \theta = \lambda/(2d_i) \quad (1)$$

Since $\lambda = V/f$, where V and f represent an ultrasonic wave speed and frequency of the generated ultrasonic waves, respectively, the equation (1) is rewritten by substituting V/f for $\lambda$ as the following equation (2):

$$\sin \theta = V/(2fd_i) \quad (2)$$

Figure 4:
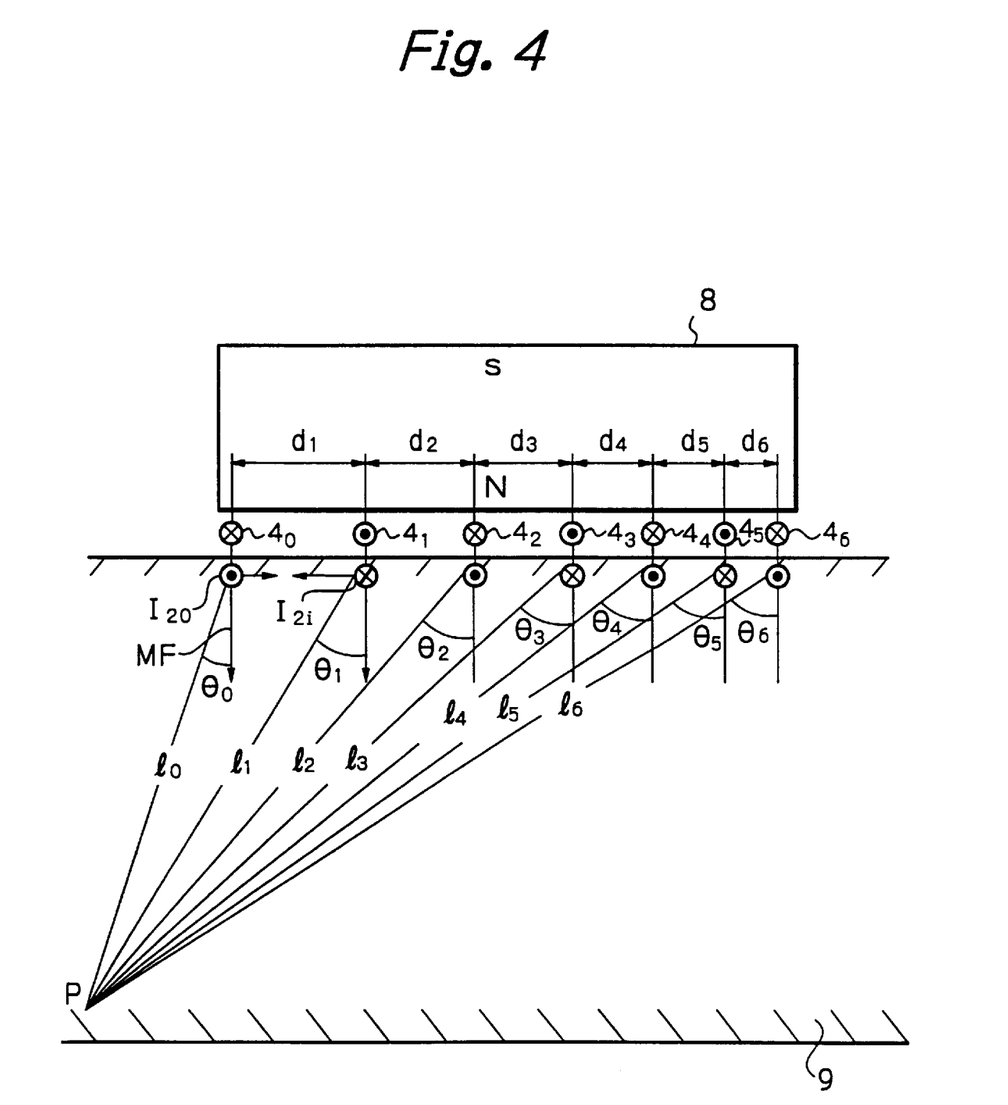

As shown in FIG. 4 and FIG. 1C, the focal type electromagnetic acoustic transducer of the present invention employs the meander coil 4, wherein the intervals $d_i$ (in FIG. 4, i=1, 2, 3, . . . ,6) between the adjacent coil segments become narrower as the coil segments are positioned further away from a focal point P, that is $d_1 < d_2 < d_3 < 1 . . . < d_6$. Therefore, the angles $\theta_i$ (in FIG. 4, i=0, 1, 2, 3 . . . ,6) are in a relationship expressed by $\theta_0 < \theta_1 < \theta_2 < \theta_3 < . . . < \theta_6$. Then, the angle $\theta$ from a line connected focus centers of the coil segments $4_i$ (in FIG. 4, i=0, 1, 2, 3, . . . ,6) to the surface of the object 9 is selected in a range of $[90°-\theta_i°]$ so that the wave fronts of the ultrasonic waves direct in the direction of the focus.

Since the ultrasonic waves generated from the adjacent coil segments $4_{i-1}$ and 4i have the 180°-different phases, the distances $l_i$ and $l_{i-1}$ and li from the respective adjacent coil segments $4_{i-1}$ and $4_i$ to the focal point P are in a relationship expressed by the following equation (3):

$$l_i - l_{i-1} = V/(2f) \quad (3)$$

Therefore, if the interval di between any adjacent coil segments is selected to satisfy the equation (3), the ultrasonic SVWs are focused at the focal point P. $\lambda = V/f$ is substituted into the equation (3) to derive the following equation (4), and thus it is capable of varying the focal point P by controlling the frequency f:

$$l_i - l_{i-1} = V/(2f) \quad (4)$$

While the foregoing embodiment shows the line focusing electromagnetic acoustic transducer which has the meander coils arranged on both surfaces of the insulation sheet 2 in parallel with each other, a point focusing electromagnetic acoustic transducer can be employed.

Figure 5A:
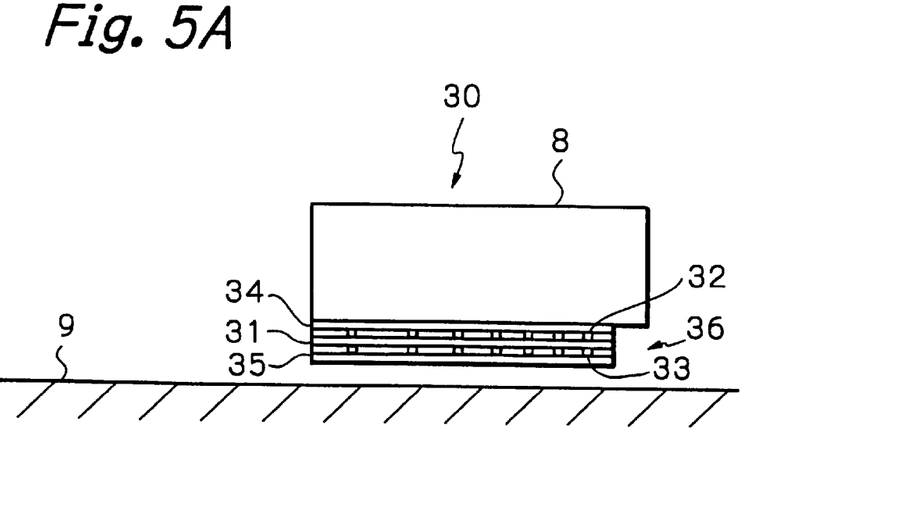
FIG. 5A is a cross-sectional view.
Figure 5B:
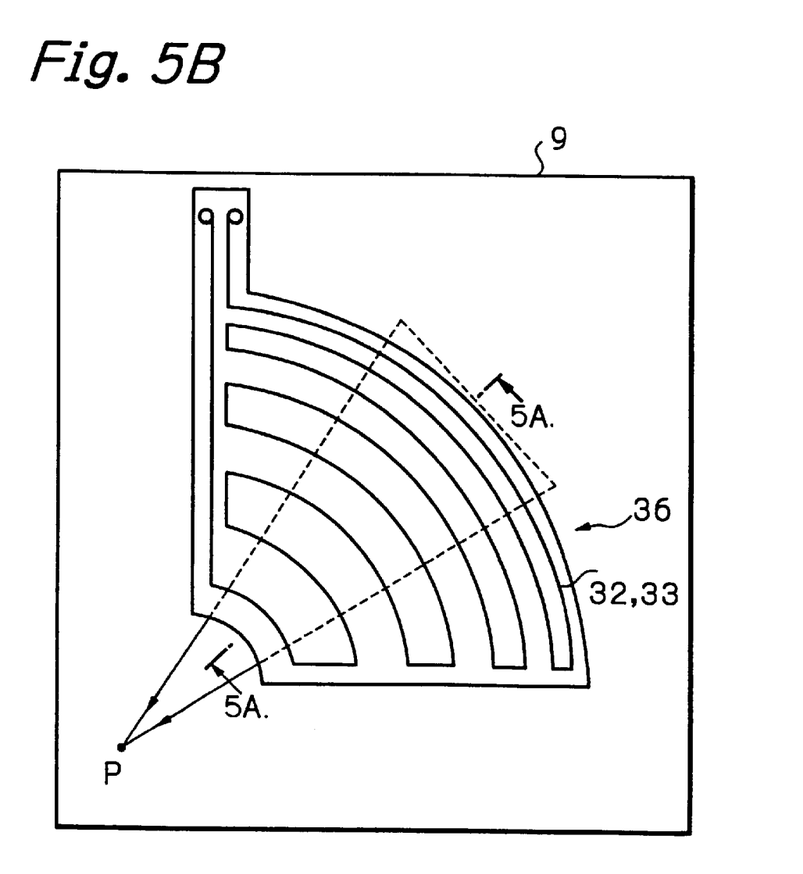
FIG. 5B is a top plan view illustrating a coil portion of the acoustic transducer.

FIG. 5 shows an embodiment of a point focusing electromagnetic acoustic transducer according to the present invention, which is referred by the numeral 30. FIG. 5A illustrates a cross-sectional view of the transducer 30, and FIG. 5B is a top plan view explanatorily illustrating a coil portion 36 on an object 9 made of a conductive material. The transducer 30 has upper and lower meander coils 32 and 33, each comprising generally sector-shaped coil segments made of a conductive material on both surfaces of an insulation sheet 31. The meander coils 32 and 33 are covered with overlying insulation sheets 34 and 35, respectively, to complete the coil portion 36. A single magnet (a permanent magnet or an electromagnet) 8 is disposed on the coil portion 36. The upper and lower meander coils 32 and 33 are positioned on the upper and lower surfaces of the insulating sheet 31 opposite to each other. Intervals between respective adjacent coil segments are sequentially varied from the center toward the outer periphery. In FIG. 5B, the interval between the innermost coil segments is the widest, and the intervals become gradually narrower toward the outer periphery.

Figure 6:
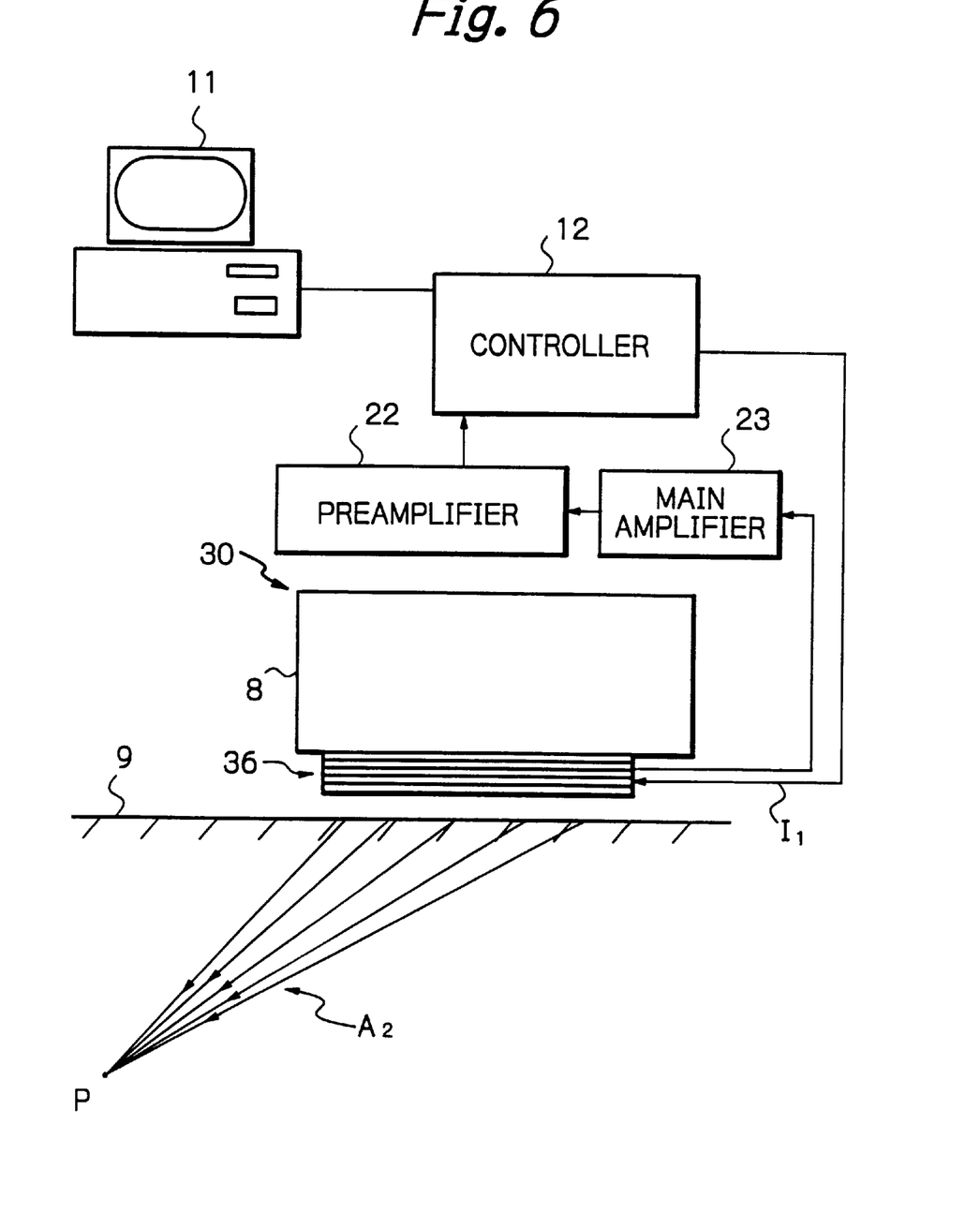
FIG. 6 is a diagram for explaining operation principles of a flaw detection system using the acoustic transducer shown in FIG. 5.

Under a flaw detection measurement of the object 9, the point focusing electromagnetic acoustic transducer 30 having the structure as described above is positioned on the object 9, as shown in FIG. 6, where the same components as those in FIG. 2 are denoted by the same reference numerals. The magnet 8 provides the static magnetic field in the depth direction of the object 9. In this state, when the lower meander coil 33 is applied with a high frequency current $I_1$ from a controller 12 under control of a personal computer 11, eddy currents are generated on the surface of the object 9 in the direction opposite to the current $I_1$. Then, Lorentz forces are produced by interactions of the eddy currents and the static magnetic field (in accordance with the Fleming's left hand rule). The Lorentz forces act on free electrons in the material composing the object 9 to cause the free electrons to collide with ions and so on, exciting motions in the object 9 vertical to the directions of the static magnet field and the eddy currents, thereby generating ultrasonic SV waves. These actions are identical to those of the aforementioned detection system illustrated in FIG. 2. However, the transducer 30 of FIG. 6 differs in that the SV waves concentrate on a single point P inside the object 9, as indicated by arrows $A_2$.

Figure 7A:
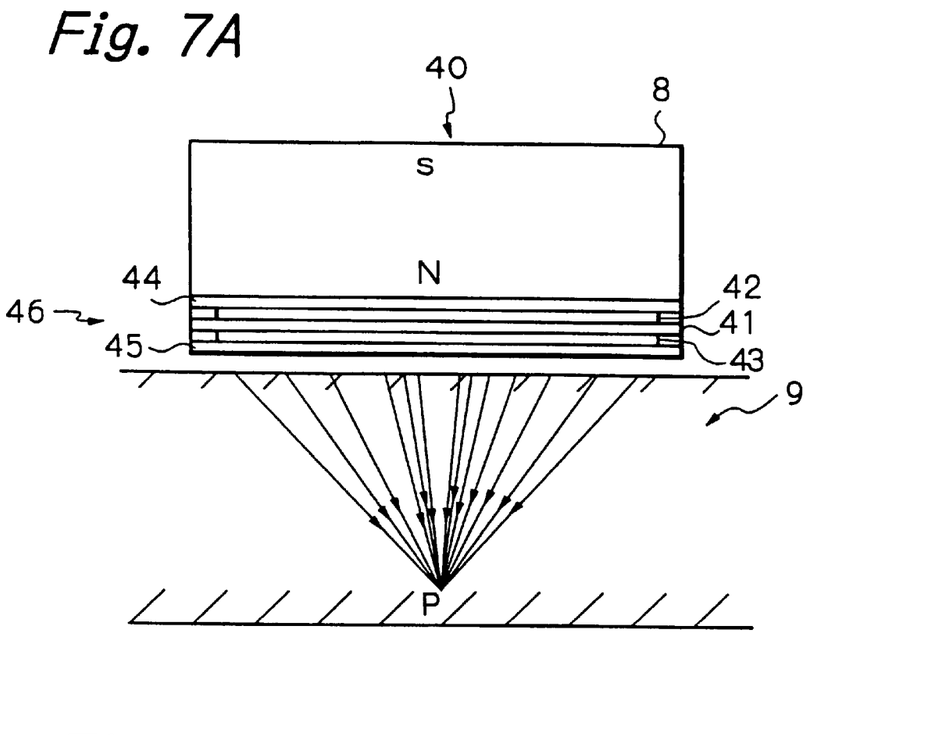
FIG. 7A is a front view of the acoustic transducer.
Figure 7B:
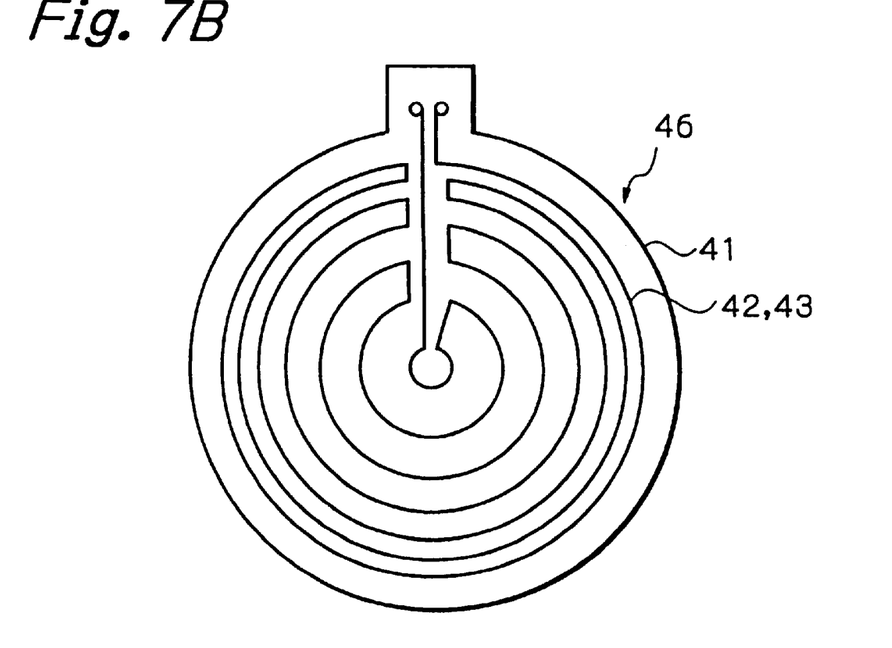
FIG. 7B is a top plan view illustrating a coil portion of the acoustic transducer.

FIGS. 7A and 7B illustrate another embodiment of a point focusing electromagnetic acoustic transducer according to the present invention, which is generally denoted by the numeral 40. FIG. 7A is a front view of the transducer, and FIG. 7B is a top plan view explanatorily illustrating a coil portion 46 of the transducer 40. The point focusing electromagnetic acoustic transducer 40 has upper and lower meander coils 42 and 43 made of a conductive material on both surfaces of an insulation sheet 41. The meander coils 42 and 43 have coil segments of concentric circular shapes. The meander coils 42 and 43 are covered with overlying insulation sheets 44 and 45, respectively, to complete the coil portion 46. A single magnet (a permanent magnet or an electromagnet) 8 is disposed on the coil portion 36. The upper and lower meander coils 42 and 43 are positioned on the upper and lower surfaces of the insulation sheet 41 opposite to each other. The intervals between respective adjacent coil segments are sequentially varied from the center toward the outer periphery. In FIG. 7B, the interval between the innermost coil segments is the widest, and the intervals become gradually narrower toward the outer periphery.

Figure 8:
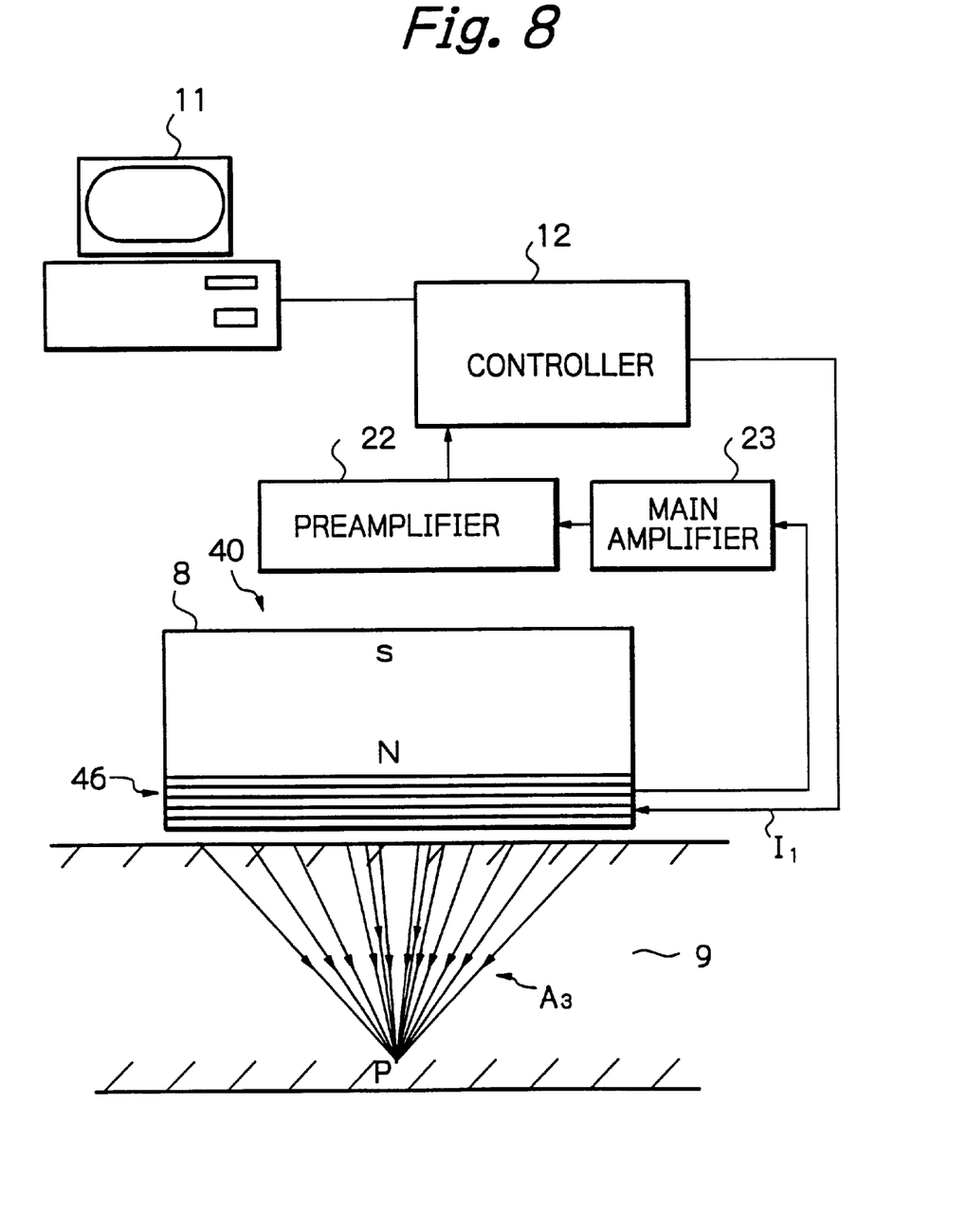
FIG. 8 is a diagram for explaining operation principles of a flaw detection system using the acoustic transducer shown in FIG. 7.

In order to detect a flaw in an object 9 of a conductive material, the point focusing electromagnetic acoustic transducer 40 illustrated in FIG. 7 is placed thereon, as illustrated in FIG. 8 showing a flaw detection system. In FIG. 8, the same components as those in FIG. 2 are referred by the same numerals. The magnet 8 forms a static magnetic field in the depth direction of the object 9. In this state, when the lower meander coil 43 is applied with a high frequency current $I_1$ from a controller 12 under control of a personal computer 11, eddy currents are generated on the surface of the object 9 in the direction opposite to the current $I_1$. Then, Lorentz forces are produced by interactions of the eddy currents and the static magnetic field (in accordance with the Fleming's left hand rule). The Lorentz forces act on free electrons in the object 9 to cause the free electrons to collide with ions and so on, exciting motions in the object 9, vertical to the directions of the static magnetic field and the eddy currents to generate ultrasonic SV waves. These actions are identical to those of the aforementioned detection system illustrated in FIG. 2. However, the transducer 40 of FIG. 8 differs in that the SV waves concentrate on a single point P inside the object 9 as indicated by arrows $A_3$.

The point focusing electromagnetic acoustic transducer illustrated in FIG. 5 or 7 is capable of focusing ultrasonic waves at one point P, and changing the point P by controlling the frequency of the current $I_1$, which is similar to the line focusing electromagnetic acoustic transducer shown in FIG. 1.

By constructing a focusing electromagnetic acoustic transducers as illustrated in FIG. 1, 5, or 7, ultrasonic SV waves can be converged to a single line or a single point of an object, thereby facilitating the detection of flaws inside the object. Also, since a radiation pattern of the SV waves from an line-array of sound sources inherently generally has a high directivity, it is possible for the SV waves to produce an extremely sharp directivity by adjusting the sound source intervals (or coil segment intervals di) to converge radiations from all sound sources to a certain point or line. It should be noted, however, that to realize a highly accurate sound source array, a sheet coil with accurately defined coil segment intervals must be used since the intervals of the meander coils dominate the frequency, as expressed in the equation (4).

A preferred example of the coil portion 7 constituting the focusing electromagnetic acoustic transducer illustrated in FIG. 1 is as follows: Each of the insulation sheets 2, 5 and 6 is made of polyimide having an external dimension with a length L=64 mm, a width W=25 mm and a thickness H=0.025 mm. Each of the upper and lower meander coils 3 and 4 is made of a copper foil and has 100 coil segments having a width $L_1$=0.11 mm. The intervals $d_i$ between the adjacent coil segments of the meander coil are varied from 0.52 mm (=$W_0$) to 1.001 mm (=$W_{98}$). The ends of the upper meander coil 3 extend or reach via a through holes at the insulation sheet 5 to terminals on the upper surface thereof, while the ends of the lower meander coil 4 extend via through holes at the insulation sheets 2 and 5 to terminals on the upper surface of the sheet 5, thereby providing electrical connections with external leads for the respective meander coils 3 and 4 on the surface of the coil portion 7. The upper and lower meander coils 3 and 4 serving as transmission and reception coils have a common ground on the upper surface of the sheet 5.

While the meander coils of the example mentioned above are preferably formed by etching copper foils deposited on both surfaces of the insulation sheet 2, the formation of meander coils is not limited to this particular manner. In an alternative, a conductive coating, for example, may be printed on both surfaces of the insulation sheet 2 to form the meander coils.

The formation of the meander coils, the provision of the connections of the ends of the meander coils with external leads, and the use of a common ground for the upper and lower meander coils can be also applied to the point focusing electromagnetic acoustic transducers illustrated in Focal. 5 and 7. Furthermore, a material of the insulation sheets is not limited to polyimide, and any other insulation material such as resin can be employed instead.

Figure 9:
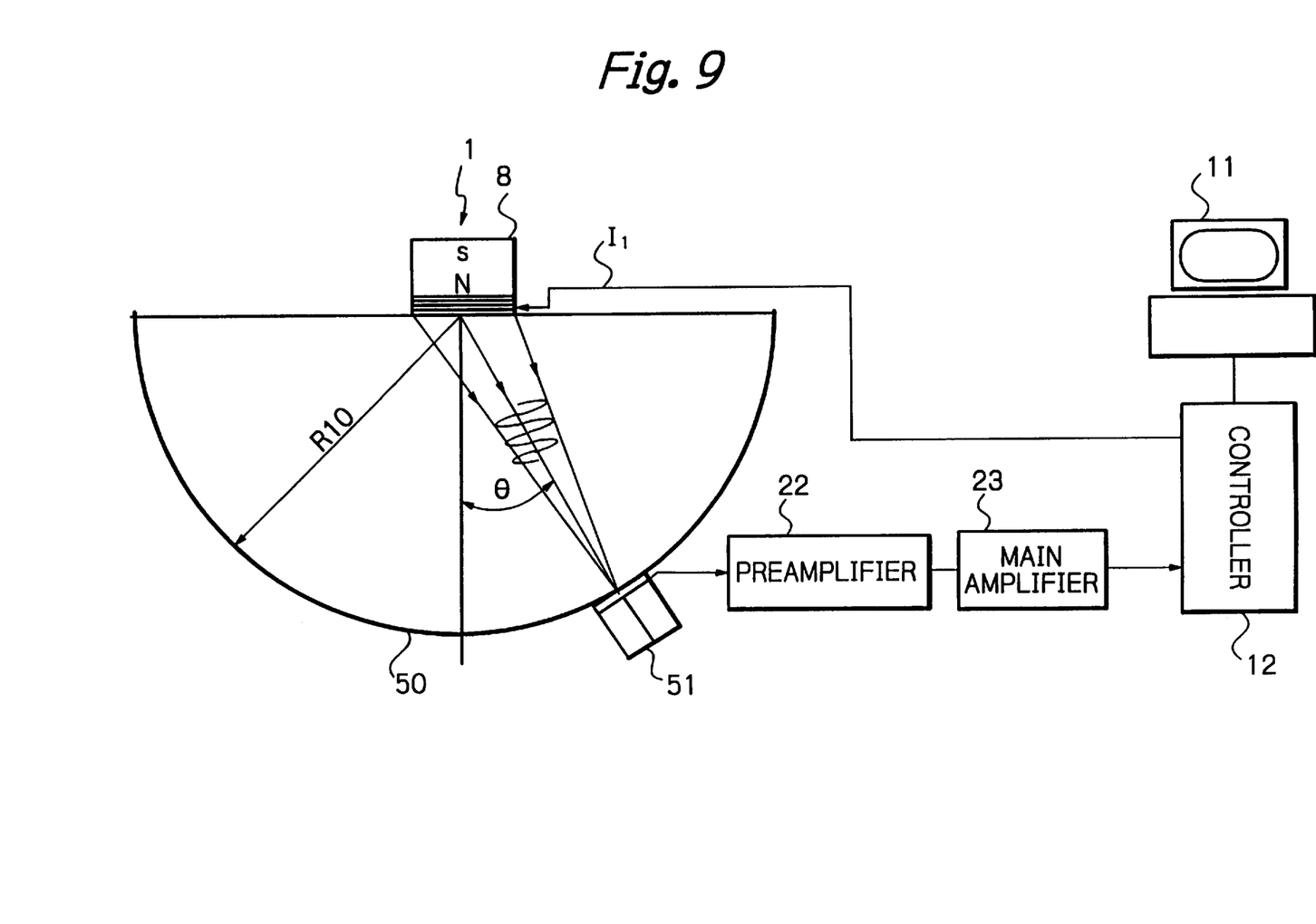
FIG. 9 is a diagram illustrating a system for measuring directivity of SV waves generated by the line focusing electromagnetic acoustic transducer shown in FIG. 1.
Figure 10:
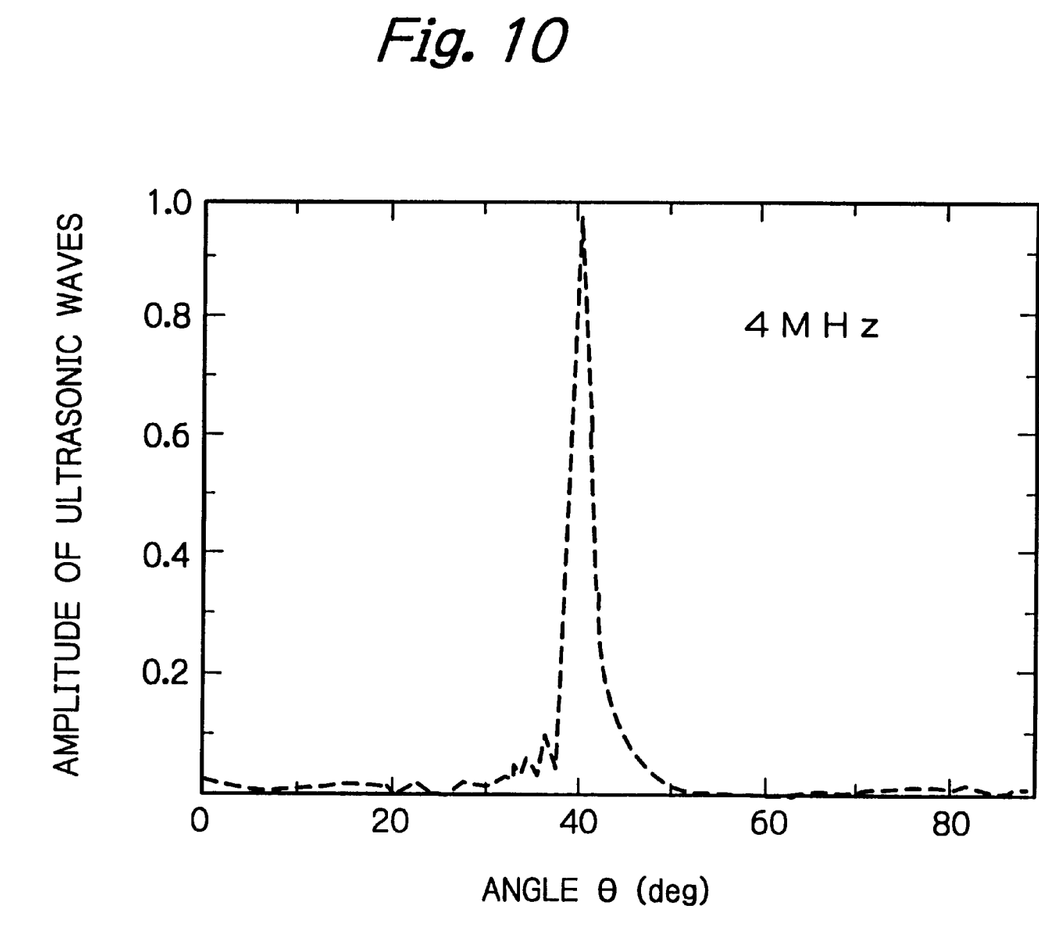
FIGS. 10–12 are graphs showing the results of SV wave directivity measurements by the system illustrated in FIG. 9.

FIG. 9 illustrates a test system for measuring the directivity of SV waves from the line focusing electromagnetic acoustic transducer 1, using the flaw detection system shown in FIG. 2, a semi-cylindrical aluminum alloy body 50 and a conventional transversal wave electromagnetic acoustic transducer 51. FIG. 10 shows the result of a measurement by the test system. Referring first to FIG. 9, the transducer 1 was placed on a chord portion of the body 50, and a high frequency current $I_1$ was applied to the transducer 1 from the controller 12 under the control of the personal computer 11 to generate ultrasonic SV waves. The conventional transversal wave electromagnetic acoustic transducer 51 was moved along the outer periphery of the aluminum alloy body 50 to detect the SV waves. The SV waves were converted to electrical signals and then provided through the preamplifier 22 and main amplifier 23 to the controller 12, where amplitudes of the signals were measured.

The current $I_1$ from the controller 12 was set to have 4 MHz frequency and the coil portion 7 employed in this transducer 1 was designed to focus SV waves of the 4 MHz at a distance of 10 cm (equal to the radius R of the semi-cylindrical body 50) from the transducer 1 and at an angle θ=40°. Referring next to FIG. 10, the ordinate in the graph represents the amplitude of the ultrasonic waves, and the abscissa represents the angle θ. As is apparent from FIG. 10, the transducer 1 exhibits a peak amplitude at θ=40°, as designed. It will be appreciated from this graph that the ultrasonic SV waves are able to be focused.

Figure 11:
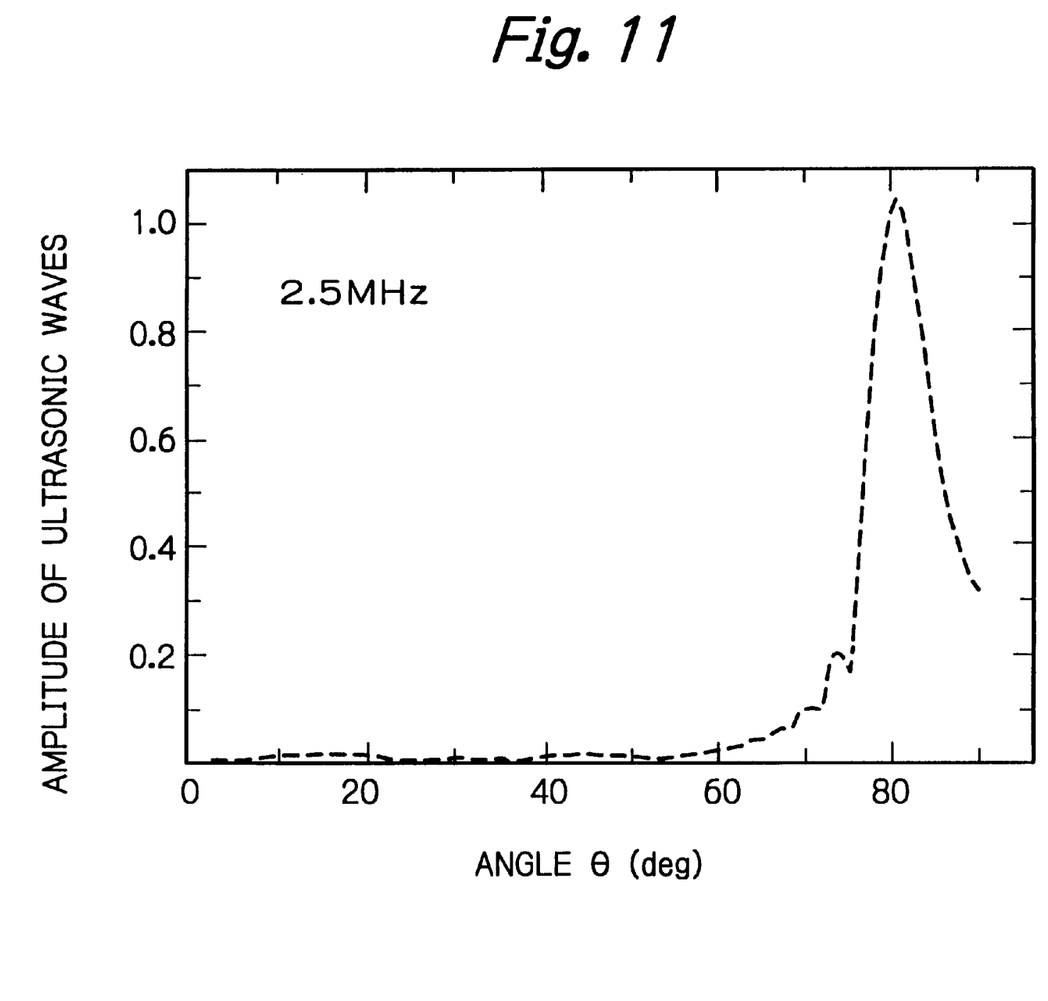
Figure 12:
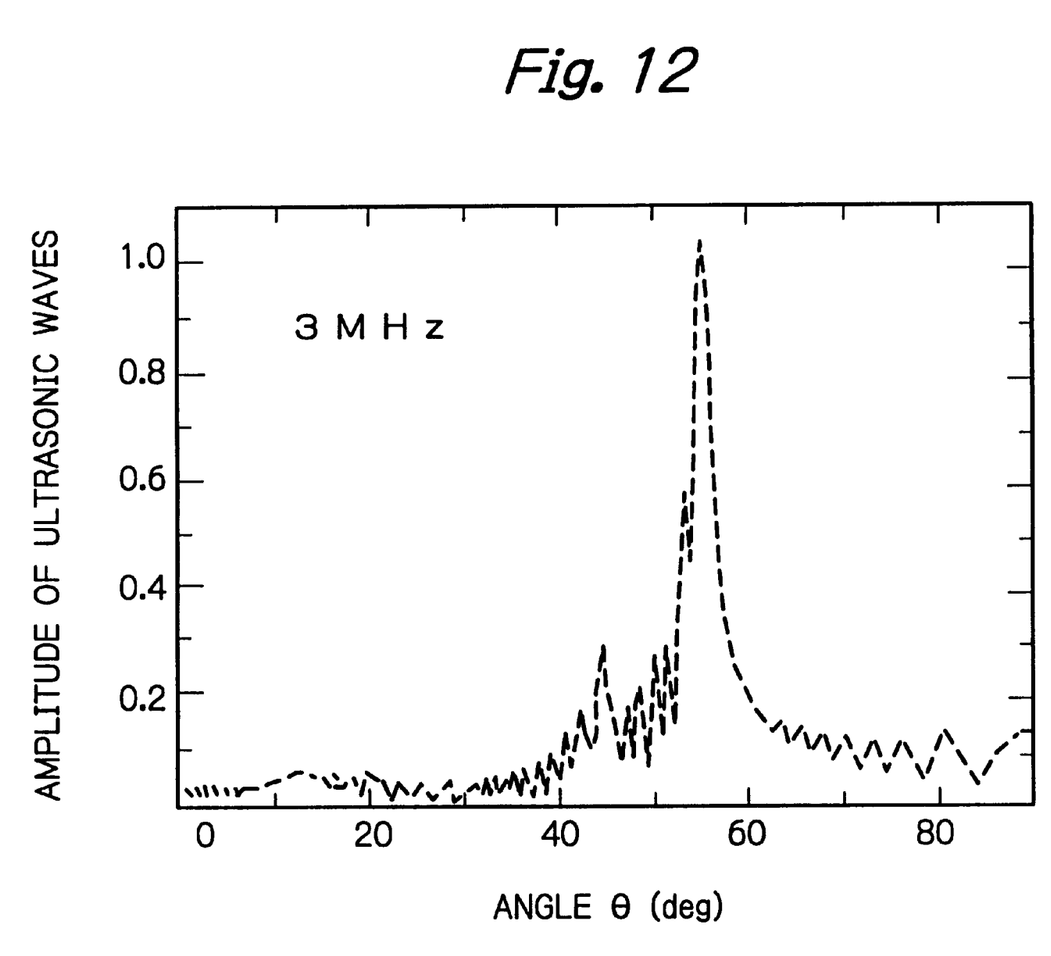

FIGS. 11 and 12 show the relationship between the amplitude of ultrasonic waves and the angle θ in the respective cases that the frequencies of the current $I_1$ or the ultrasonic waves were set at 2.5 MHz and 3 MHz, respectively. A peak is indicated at θ=80° when the frequency was at 2.5 MHz as illustrated in FIG. 11, while a peak is indicated at θ=55° when the frequency was at 3 MHz as illustrated in FIG. 12. These graphs show that the focal position can be varied by changing the frequency of the current $I_1$.

Figure 13A:
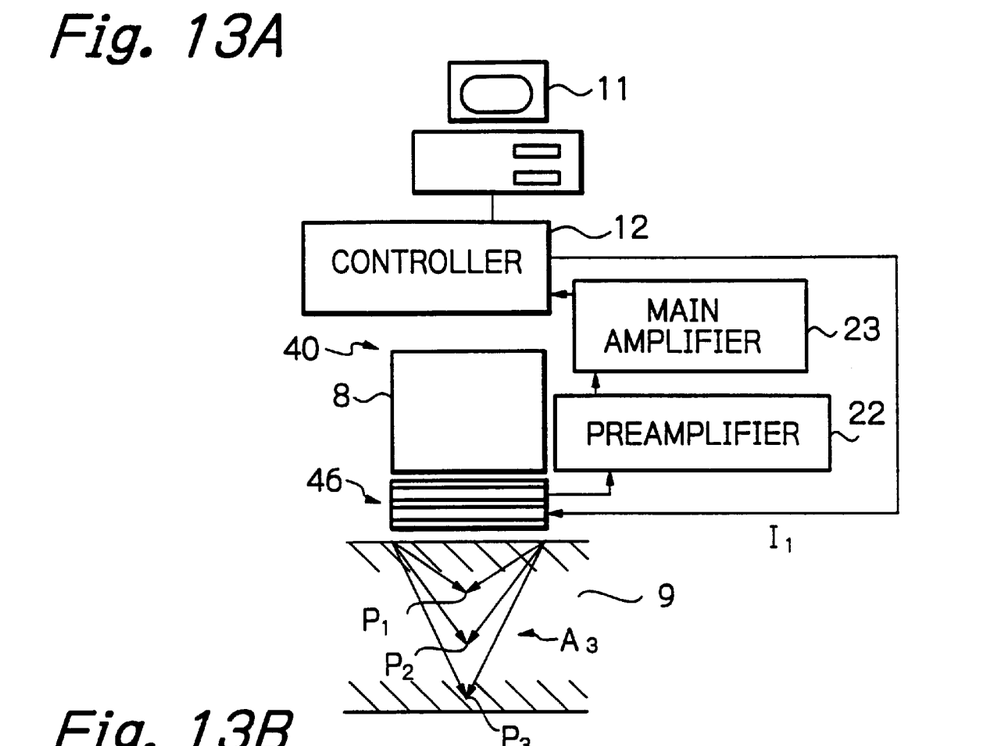
FIGS. 13A and 13B are diagrams for explaining a flaw detection system using the acoustic transducer shown in FIG. 5 or 7.
Figure 13B:
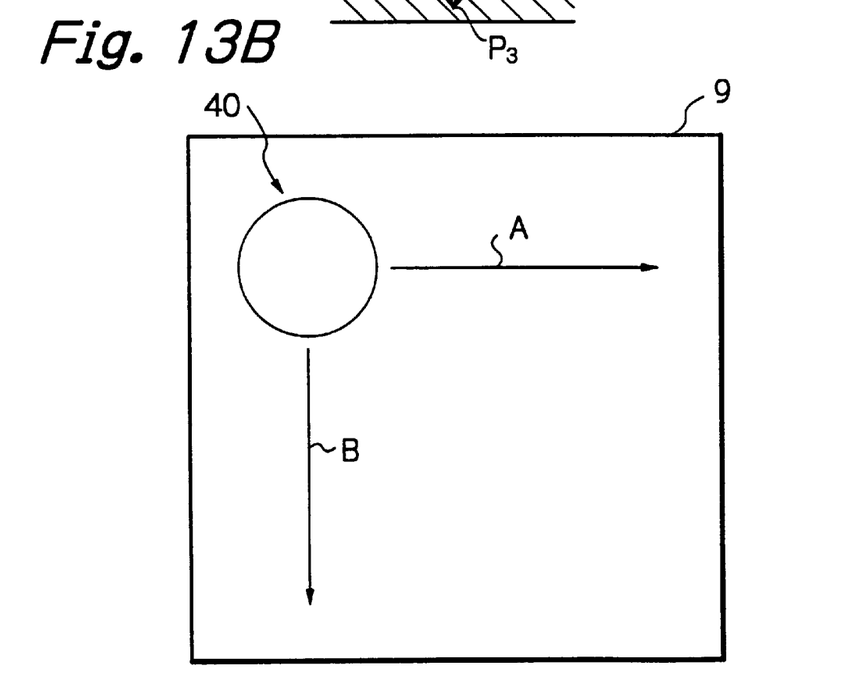

By referring to FIGS. 13A and 13B, there will next be explained, in more detail, a flaw detection method executed in the system sown in FIG. 8 including the point focusing electromagnetic acoustic transducer 46. As illustrated in FIG. 13A, the transducer 46 is placed on the object 9, and applied with a high frequency current $I_1$ from the controller 12 under the control of the personal computer 11 to generate ultrasonic SV waves. By changing the frequency of the current $I_1$, the SV waves are focused at focal points $P_1$, $P_2$, $P_3$ in the depth direction of the object 9. Assuming that the frequencies at which the SV waves are focused at the focal point $P_1$, $P_2$, $P_3$ are $f_1$, $f_2$, $f_3$, respectively, $f_3 > f_2 > f_1$ is satisfied. By scanning the transducer 46 in directions A and B on the object 9 as illustrated in FIG. 13B, it is possible to three-dimensionally detect flaws in the object 9.

The focusing electromagnetic acoustic transducer according to the present invention can provide improved performance (for example, the capabilities of high frequency transmission and reception with reduced noise), stable quality, and reduction in size and weight, which cannot be realized by conventional transducers. Thus, the focal type electromagnetic acoustic transducer according to the present invention can advantageously realize an extremely sharp directivity as compared with SH waves generated by conventional focal type electromagnetic acoustic transducers. In addition, highly accurate flaw detection in the thickness direction of an object can be also accomplished by changing the frequency of the high frequency burst waves.

While preferred embodiments have been described using specific terms, it is to be understood that changes and variations will be made without departing from the spirit or scope of the following claims.

What is claimed is:

1. A focusing electromagnetic acoustic transducer comprising:

a first insulation sheet;

a first meander coil formed on a first surface of said first insulation sheet, a second meander coil formed on a second surface of said first insulation sheet, said first and second meander coils positioned so as to be coincident with each other, each of said meander coils comprising a plurality of coil segments wherein intervals between adjacent coil segments vary sequentially from one end to another end of said meander coils;

a second insulation sheet attached to said first meander coil so as to sandwich the first meander coil between said first and second insulation sheets, a third insulation sheet attached to said second meander coil so as to sandwich the second meander coil between said first and third insulation sheets; and a magnet having opposite surfaces exhibiting opposite magnetic poles, one of said opposite surfaces being, positioned above said second insulation sheet.

2. A transducer according to claim 1, wherein said coil segments ot each of said meander coils are straight lines parallel to each other so that said transducer operates as a line focusing electromagnetic acoustic transducer.

3. A transducer according to claim 1, wherein said coil segments ot each of said meander coils are sector shapes on respective circles having a center point in common so that said transducer operates as a point focusing electromagnetic acoustic transducer.

4. A transducer according to claim 1, wherein said coil segments of each of said meander coils are generally circular shapes having a center point in common so that said transducer operates as a point focusing electromagnetic acoustic transducer.

5. A transducer according to claim 1, wherein:
one of said meander coils is configured to transmit acoustic waves and the other is configured to detect acoustic waves, and
said meander coils having ends which extend through holes formed in said first and second insulation sheets to connection terminals on one of the surfaces of said second insulation sheet one of said terminals being a common ground terminal for said meander coils.

6. A system according to claim 1, wherein all ends of said meander coils extend through holes formed in said first and second insulation sheets to connection terminals on one of the surfaces of said second insulation sheet, one of said terminals being a common ground terminal for said meander coils.

7. A system for detecting a flaw in an object comprising:
a focusing electromagnetic acoustic transducer to be placed on said object comprising:
a first insulation sheet;
a first meander coil formed on a first surface of said first insulation sheet;
a second meander coil formed on a second surface of said first insulation sheet, said first and second meander coils positioned so as to be coincident with each other, each of said meander coils comprising a plurality of coil segments wherein intervals between adjacent coil segments vary sequentially from one end to another end of said meander coils;
a second insulation sheet attached to said first meander coil so as to sandwich the first meander coil between said first and second insulation sheets;
a third insulation sheet attached to said second meander coil so as to sandwich the second meander coil between said first and third insulation sheets;
a magnet having opposite surfaces exhibiting,, opposite magnetic poles, said opposite surfaces being positioned above said second insulation sheet, a source configured to supply a high frequency current to one of said meander coils to transmit ultrasonic SV waves into said object the frequency of said current being variable to vary a focal point in said object; and
a detection mechanism configured to detect a flaw in said object in accordance with amplitudes and phases of signals detected by the other meander coil.

8. A system according to claim 7, wherein said coil segments of each of said meander coils are straight lines parallel to each other so that said transducer operates as a line focusing, electromagnetic acoustic transducer.

9. A system according to claim 7, wherein said coil segments of each of said meander coils are sector shapes on respective circles having a center point in common so that said transducer operates as a point focusing electromagnetic acoustic transducer.

10. A system according to claim 6, wherein said coil segments of each of said meander coils are generally circular shapes having a center point in common so that said transducer operates as a point focusing electromagnetic acoustic transducer.

11. A method of detecting a flaw in an object comprising the steps of:
preparing, a focusing electromagnetic acoustic transducer having transmission and reception meander coils;
placing said transducer on said object;
supplying a high frequency current to said transmission meander coil to transmit ultrasonic SV waves into said object;
varying the frequency of said current in time sequence thereby changing a position of a focal point of said transducer; and
detecting a flaw in said object in accordance with amplitudes and phases of signals detected by said reception meander coil.

12. A method according to claim 11, wherein said focusing electromagnetic acoustic transducer comprises:
a first insulation sheet;
a first meander coil formed on a first surface of said first insulation sheet;
a second meander coil formed on a second surface of said first insulation sheet, said first and second meander coils positioned so as to be coincident with each other, each of said meander coils comprising a plurality of coil segments wherein intervals between adjacent coil segments vary sequentially from one end to another end of said meander coils;
a second insulation sheet attached to said first meander coil so as to sandwich the first meander coil between said first and second insulation sheets;
a third insulation sheet attached to said second meander coil so as to sandwich the second meander coil between said first and third insulation sheets; and
a magnet having opposite surfaces exhibiting opposite magnetic poles said opposite surfaces being positioned above said second insulation sheet.

13. A method according to claim 11, wherein said coil segments of each of said meander coils are straight lines parallel to each other so that said transducer operates as a line focusing, electromagnetic acoustic transducer.

14. A method according to claim 11, wherein said coil segments of each of said meander coils are sector shapes on respective circles having a center point in common so that said transducer operates as a point focusing electromagnetic acoustic transducer.

15. A method according to claim 11, wherein said coil segments of each of said meander coils are generally circular shapes having a center point in common so that said transducer operates as a point focusing, electromagnetic acoustic transducer.

16. A method according to claim 11, wherein:
one of said meander coils is configured to transmit ultrasonic waves and the other is configured to detect ultrasonic waves, and
said meander coils having ends which extend through holes formed in said first and second insulation sheets to connection terminals on one of the surfaces of said second insulation sheet, one of said terminals being a common ground terminal for said meander coils.

* * * * *